United States Patent [19]

Cormack et al.

[11] Patent Number: 4,872,757
[45] Date of Patent: Oct. 10, 1989

[54] OPTICAL CONVEX SURFACE PROFILING AND GAUGING APPARATUS AND METHOD THEREFOR

[75] Inventors: Robert H. Cormack, Boulder; Carey S. Brown, Denver, both of Colo.

[73] Assignee: Ball Corporation, Muncie, Ind.

[21] Appl. No.: 183,763

[22] Filed: Apr. 20, 1988

[51] Int. Cl.⁴ .............................................. G01B 11/24
[52] U.S. Cl. .................................... 356/376; 356/237; 356/428; 358/106
[58] Field of Search ............... 356/376, 237, 426, 428; 382/8; 358/101, 106; 209/577, 585, 597, 598

[56]  References Cited

U.S. PATENT DOCUMENTS

| | | | |
|---|---|---|---|
| 3,666,885 | 5/1972 | Hemsley et al. | 178/6.8 |
| 3,826,576 | 7/1974 | Stewart | 356/384 |
| 4,021,119 | 5/1977 | Stauffer | 356/386 |
| 4,162,126 | 7/1979 | Nakagawa et al. | 356/237 |
| 4,226,539 | 10/1980 | Nakagawa et al. | 356/445 |
| 4,298,285 | 11/1981 | Ito | 356/376 |
| 4,326,808 | 4/1982 | Pryor et al. | 356/445 |
| 4,410,278 | 10/1983 | Makihira et al. | 356/445 |
| 4,465,937 | 8/1984 | Forbes | 250/560 |
| 4,476,533 | 10/1984 | Daudt et al. | 364/473 |
| 4,576,482 | 3/1986 | Pryor | 356/376 |
| 4,629,319 | 12/1986 | Clarke et al. | 356/237 |
| 4,675,730 | 6/1987 | Adomaitis et al. | 358/106 |
| 4,676,648 | 6/1987 | Schulz et al. | 356/426 |

Primary Examiner—F. L. Evans
Attorney, Agent, or Firm—Dorr, Carson, Sloan & Peterson

[57] ABSTRACT

The present invention utilizes back lighting optics to produce converging white light over an area larger than an area of the edge of the convex object being profiled by the present invention. Opposite the back lighting optics are located a shadow image detector which detects the shadow image of the edge of the convex object, which is located between the back lighting optics and the shadow image detector. The detector generates a plurality of pixel outputs from each of a plurality of vertical locations for the shadow image of the edge. A rotating stage provides relative movement between the convex object and the detector/optics arrangement. The output of the detector which is a high resolution camera is fed into a data processing system which determins a sub-pixel distance measurement for each of the plurality of vertical locations and arranges the sub-pixel distance measurements into rows and columns to construct a surface profile of the convex object.

12 Claims, 8 Drawing Sheets

OPTICAL CONVEX SURFACE PROFILING AND GAUGING APPARATUS AND METHOD THEREFOR

BACKGROUND OF THE INVENTION

1. Field of the Invention

The present invention relates to systems and methods for optically profiling and gauging convex surfaces of objects and, in particular, the present invention relates to optical non-contact profiling of the convex surface of objects wherein the object is back lit with converging white light and the resulting shadow image edges are detected and analyzed.

2. Background of Prior Art

There is a need in industry to profile the convex surfaces of objects to ascertain the presence of defects, to aid in the understanding of the manufacturing or shipping processes on the object, or to better analyze the material properties of the object.

For example, aluminum beverage cans are objects having a convex surface around their entire cylindrical sidewall which may be as thin as 0.005 inches. Conventional surface profiling techniques can provide precise measurements of unfilled beverage cans utilizing contact techniques, but such techniques are principally limited to the measurement of the top edge and bottom edge of the sidewall since contact with the center thin sidewalls of the can may cause deflection and, therefore, error in measurement. Hence, a need exists to profile the surface of aluminum beverage cans and to provide accurate metrology of the entire can sidewalls so that important information concerning the measurement and quantification of defects such as dents, may be obtained. Such information provides valuable feedback in understanding, evaluating, and adjusting the manufacturing processes to form the can as well as providing information concerning the material properties of the aluminum in such manufacturing processes.

While the present invention is generally directed towards the surface profiling of aluminum beverage cans, it is to be expressly understood that any convex surface or portion thereof of an object or work piece could be likewise evaluated under the teachings of the present invention.

A number of prior art patented approaches are available for surface profiling such as the following which all relate to an optical reflection technique wherein light, usually a laser beam, is reflected off of the surface of the object. The reflected light is then analyzed. Examples of reflected light approaches are as follows.

U.S. Pat. No. 4,629,319 by Clarke et al. sets forth an invention for the electro-optical sensing of defects such as dents, creases, low spots and flat spots on the surface of sheet metal or plastic panels such as those used on the hoods and fenders of cars, refrigerators and furniture. Clarke directs light onto the surface. The light reflected from the surface impinges upon a retroreflective member to return the reflected light to the surface area to be re-reflected. The re-reflected light is then imaged and carries information as to the nature of the defect.

U.S. Pat. No. 4,326,808 issued to Pryor et al. sets forth an apparatus for determining defects in the outer surface of an elongated object wherein the object to be inspected passes through an aperture of a conical mirror surface. The light is directed onto the mirror surface, reflected by the object, imaged and then analyzed to determine the nature of the defect.

U.S. Pat. No. 4,675,730 issued to Adomaitis sets forth an apparatus for continuously inspecting the surface of a moving object for defects. The surface of the object is illuminated with both specular and/or diffused light of selected wavelengths. The moving surface is rendered momentarily motionless and a plurality of sensors located to view the width of the object detects the presence of the defects. An electronic image of the defect contains gray scale levels that represent varying intensities of the light reflected by the defect. A comparison is then made with a defect free image and, if different, then a freeze frame analysis of the object is made.

U.S. Pat. No. 4,410,278 issued to Makihira et al. sets forth an apparatus for inspecting the outer peripheral surface of a cylindrical object. The light, in slit form, is projected on the surface of the cylindrical object. The reflected light is detected by a photo detector and is quantized at threshold values higher or lower than an average level. The three types of surface defects of a chip, a crack, and a pit are separately detected and identified.

U.S. Pat. No. 4,226,539 issued to Nakagawa et al. also sets forth a system for cylindrical body surface inspection. The cylindrical body is rotated around its axis at a constant speed. Light is directed onto the surface of the body and an optical detector detects the reflected light indicative of a surface condition of a small width baseline which is parallel to the axis of the cylindrical body. A sampling detection repeats as the body rotates to scan the entire surface of the cylinder.

U.S. Pat. No. 4,162,126 issued to Nakagawa et al. sets forth a camera system which senses diffused reflected light from the surface of an object in order to analyze the reflected light wherein a threshold level is used so that surface defect patterns such as a broken cavity, a pit, or a crack pattern can be selectively discriminated.

All of the above represent prior approaches for surface profiling and gauging involve a non-contacting system like the present invention. However, each of these approaches analyze light which is reflected from the surface and they are suitable for evaluating concave surfaces. The present invention does not reflect light nor does it analyze the reflected light.

The following prior art approaches set forth in inspection techinques which analyze the shadow of the object being inspected.

U.S. Pat. No. 4,576,482 issued to Pryor sets forth an apparatus for determining accurate dimensions of individual work pieces. The apparatus is a non-contacting system wherein a collimated or semi-collimated light source illuminates at least one edge of the work piece with parallel light rays so that a lens can form an image of the illuminated edge. This image provides an average shadow over an area of the edge. An array of photosensitive elements such as photodiodes produce an electrical signal in response to the light impacting thereon. The edge image as sensed by the photodiode array can then be analyzed to provide a determination of a dimension such as length, squareness, curvature and the like.

The 1972 patent to Hemsley (U.S. Pat. No. 3,666,885) utilizes a strobe for directing a short duration light pulse onto the object to form a shadow image of the object in a camera. The camera is modified for single line scanning and produces a line waveform of the shadow image. The Hemsley approach is adaptable for either hot or cold objects being scanned. Hemsley utilizes a referenced object to determine the initial measurement and then compares the object being inspected to the measured value and records any differences in the line waveforms.

The 1984 patent to Forbes (U.S. Pat. No. 4,465,937) utilizes a light source mounted in a scanning head that is rotated about the object and which can be advanced along the length of the object to provide data pertaining to the entire peripheral surface of the object. Forbes utilizes a light source that provides a beam of light having a width greater than the width of the object being scanned so that as the light source is rotated around the object, deviations in the shadow's edge can be sensed by photo sensors and determined.

The 1984 patent to Daudt (U.S. Pat. No. 4,476,533) pertains to a non-contact optical gauger for measuring hot glassware articles while being manufactured. The system makes specific measurements of height, perpendicular, neck diameter, and height variation of the glassware article. Articles falling outside predetermined measurements are rejected.

The above prior art approaches for surface profiling involve a non-contacting system utilizing the shadow image from light projected onto the object. The present invention is similar to these approaches but substantially improves upon them. The present invention optically creates a plurality of knife-edge shadows of the convex surface of an object without the generation of error causing glints as the surface is rotated and then digitally analyzes the edges. The present invention utilizes converging white light in a reduced field of view and is automatically capable of creating from the plurality of edges a dense array of topological data having 2000 to 5000 individual data points per inch for the surface of an object being profiled without distorting the surface of the object through contact. The cylindrical telescope of the present invention narrows the field of view in the horizontal direction of the shadow image to magnify the presence of defects. This increases the accuracy of sub-pixel analysis of the present invention.

SUMMARY OF THE INVENTION

The present invention, therefore, automatically creates a dense topological data array for the surface of the object being profiled without distorting the object through contact.

The present invention utilizes back lighting optics to produce converging white light over an area larger than an area of the edge of the convex object being profiled by the present invention. Opposite the back lighting optics is located a shadow image detector which detects the shadow image of the edge of the convex object. The object is located between the back lighting optics and the shadow image detector. The detector generates a plurality of pixel outputs from each of a plurality of discrete vertical locations on the shadow image of the edge. A rotating stage provides relative movement between the convex object and the detector/optics arrangement. The output of the detector which is a high resolution camera is fed into a data processing system which determines a sub-pixel distance measurement for each of the plurality of vertical locations and arranges the sub-pixel distance measurements into rows and columns to construct a surface profile of the convex object.

Figure 1:
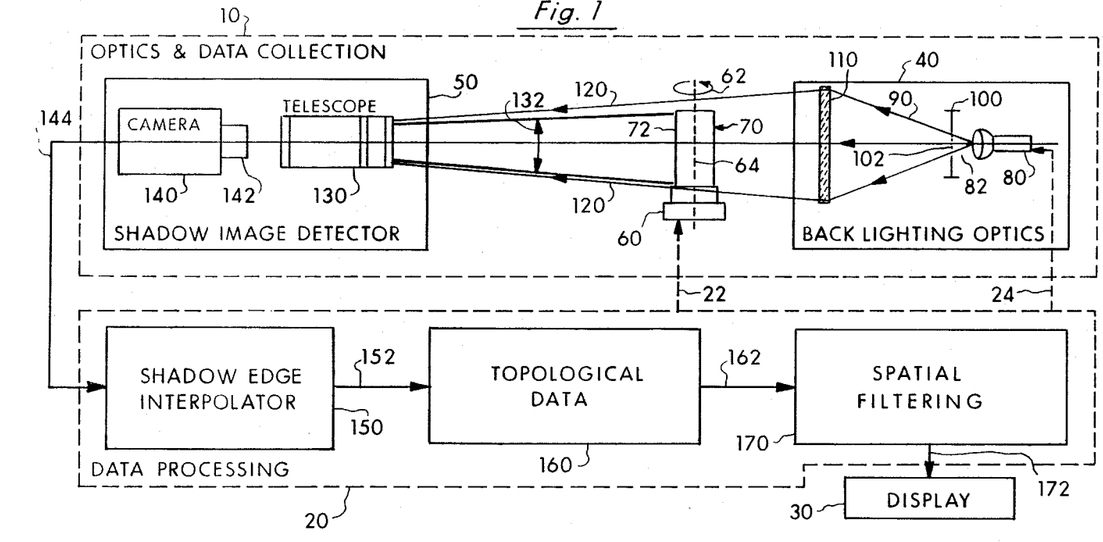
FIG. 1 sets forth, in block diagram format, the components of the surface profiling system of the present invention.
Figure 2:
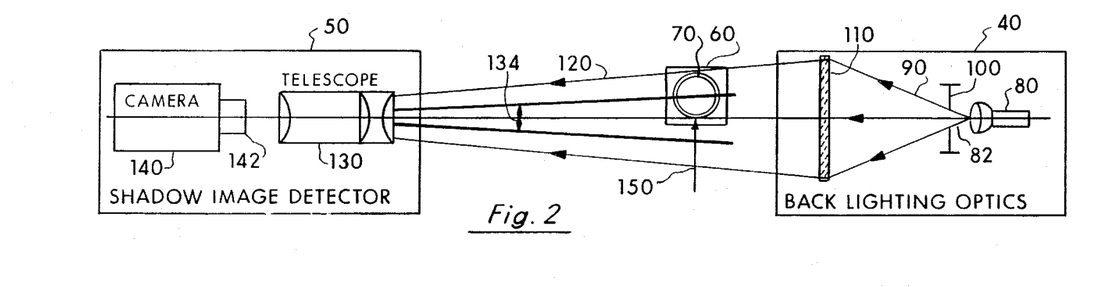
FIG. 2 is a top view of the optics and data collection shown in FIG. 1.

In FIGS. 1 and 2, the surface profiling system of the present invention is generally set forth to include three major functional portions. The optics and data collection portion 10, the data processing portion 20, and the display portion 30.

The optics and data collection portion 10 contains the back lighting optics 40, the shadow image detector 50, and a rotating stage 60. An object 70 having a convex shaped surface, such as an aluminum beverage can, is placed on the rotating stage 60 between the lighting optics 40 and the shadow image detector 50. The rotating platform or stage 60 causes the convex surface 72 of the object 70 to be rotated in the direction of arrow 62. The rotating stage 60, in the preferred embodiment, is driven by a stepper motor which provides rotation to the convex surface of the object 62 in a range of 10 seconds to 4 minutes per rotation. The rotating stage 60 could also be driven by a synchronous motor or other type of drive to provide the rotation 62. It is to be expressly understood that the optics and data collection 10 could be designed such that the back lighting optics 40 and shadow image detector 50 would rotate about a stationary stage 60. Such an approach as well as the rotation of stage 60 provides relative movement between the optics 40/detector 50 and the object 70 as required under the teachings of the present invention.

The back lighting optics 40 includes a light source 80 which is any concentrated source of white light such as from a projector bulb, a fiber optic source, a strobe light or the like. The white light 82 from the light source 80 is directed through an iris 100 which contains a frosted glass diffuser 102. The iris 100 functions to reduce the number of ray directions for the light 120 after it passes through the lens 110. Hence, the size of the circular aperture for the diffuser 102 is such that it effectively provides a substantial point source for light 90.

The light 90 is delivered into a field lens 110 which, in the preferable embodiment, is a Fresnel lens which converges the white light 120 and delivers it towards the object 70, into a cylindrical telescope 130 and then into a camera 140. The lens 110 must be bigger than the object 70 and captures the rays 90 from the iris 100 for delivery into the telescope 130.

The optics and data collection system 10 are adjusted so that the camera 140 receives a sharp, high contrast shadow of the edge or edges of the object 70. In the preferred embodiment, the light source 80 is a fiber optic cable connected to a remote light source. The distance from the end of the cable (i.e., light source 80) to the iris 100 is 2.5 inches. The iris 70 is capable of being opened to two inches in diameter with a centrally located diffuser 102. The iris 100 is adjusted to as small an opening as possible, such as one inch, consistent with uniform illumination of the camera field of view. The Fresnel lens 110 is Model No. 34-7781 from Ealing Electro Optics Corp. and is a 14 inch F.L., 200 lines-/inch, 11.5 inches square. The Fresnel lens 110 is located 19.75 inches from the iris 70.

Figure 3:
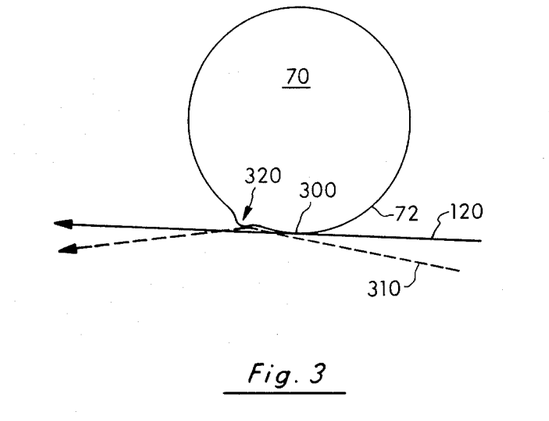
FIG. 3 is an illustration of the generation of the shadow's edge through use of coverging light.

The converged white light 120 produced by the back lighting optics 40 is uniformly produced and insures that the shadow image detector 50 will not see glints from the convex surface 72 on the object 70 so that the shadow edge detected fully represents the accurate surface profile of the object 70. For example, in FIG. 3, which is a view from the top of the object 70, the converging white light 120 passes the edge 300 of the convex surface 72 of the can 70. If too many ray directions were present in the lighting (e.g., if iris 100 were adjusted too large), then additional rays, e.g., ray 310, would cause false readings due to the reflections off of surface irregularities or defects such as bump 320. The produced white light 120 covers an area larger than the area of the edge 300 so that the edge 300 is uniformly illuminated.

The telescope 130 in the shadow image detector 50 is an afocal (Keplerian) cylindrical lens telescope which is used to reduce or compress the field of view perpendicular to the rotation axis (i.e., the horizontal direction on the shadow image) 62 of the object 70. As shown in FIG. 1, the vertical field of view 132 is such as to take in the entire height of the object 70. As shown in FIG. 2, the horizontal field of view 134 is such to concentrate on the edge 150 of the object being analyzed. In the preferred embodiment, the field telescope provides a field of view 134 which is at least one half the field of view 132. This magnifies the surface area of the edge 300 of the object in the horizontal direction at least twice that in the vertical direction. This is important, since decreasing the field of view 134 over the field of view 132 emphasizes the presence of surface irregularities at edge 300. Any suitable magnification such as 2:1, 3:1 or the like could be used under the teachings of the present invention.

Figure 4:
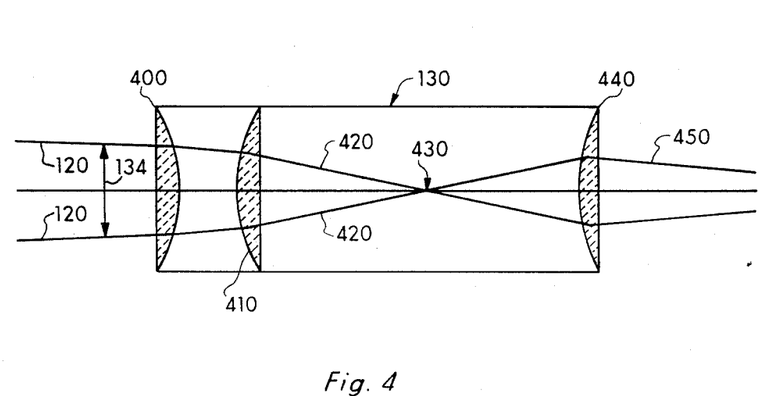
FIG. 4 is an illustration showing the field of view compression of the cylindrical telescope, FIG. 5 sets forth the column arrangement for the rotating convex object, FIG. 6 sets forth the row arrangement for the rotating convex object.

In FIG. 4, the top view of telescope 130 is shown to illustrate the field of view 134. The converging light 120 is delivered into a first cylindrical lens 400 and then into a second cylindrical lens 410 after which the light 420 passes through a focal point 430 before being extended through a third lens 440. The light 450 is then delivered into the camera 140.

In the preferred embodiment, the lens 400 of the telescope 130 is located 37.5 inches from the Fresnel lens 110 or 28.5 inches from the center 64 of the object 70. The center 64 of the object 70, therefore, is located 7 inches from the Fresnel lens 110. Lens 410 is located 5.50 inches from lens 400 and lens 440 is located 8.50 inches from lens 410. Lens 400 is 250 mm F.L., 2 inches square, lens 410 is 250 mm F.L., 2 inches square, and lens 440 is 80 mm F.L., 2 inches square.

A high quality camera 140 is used such as a CCD Array camera made by Sony as Model No. XC-77. The camera incorporates a high quality lens 142 such as a Fuji Television 50 mm lens. The lens 142 is connected to the camera 140 and is located 0.75 inches from lens 440.

Further, the light source intensity and lens FSTOP of the camera are adjusted so that the light-to-dark transition of the shadow image of edge 300 spatially covers at least four to five pixels on the camera's detector and, in intensity, spans substantially all of the dynamic range of the camera. The entire light-dark intensity range is used. As will be pointed out later, this setting of the camera increases the accuracy and decreases the noise in the subsequent data processing steps.

In setting up the optics and data collection system 10 of the present invention, the camera 140 is placed at the focal point of the field or Fresnel lens 110. The back lighting optics 40 are then adjusted so that the camera detects a uniform field of white around the object. The telescope 130 is then inserted.

The data processing system 20 of the present invention receives the camera output 144 and processes the output to provide the various displays 30 of the present invention.

The first step in processing the shadow images 144 from the camera 140 is to locate the edge of the shadow to much less than one pixel. This is performed by the shadow edge interpolator 150. Accuracies of up to one/sixty fourth of a pixel have been obtained with the accuracy being limited only by the non-uniformity of the back lighting 120 and camera 140 noise. The sub-pixel shadow locations 152 are arranged into topological data 160 which is an X-Y (row-column) data array. The topological data 160 represents the topological structure of the object surface in sub-pixel values. Each column in the data array is a surface profile of edge 300 parallel to the axis 64 of rotation of the object 70. Each row of data represents a circumferential profile around one complete revolution or, in some cases, a partial revolution.

The X-Y topological data array 162 is then spatially filtered 170 for display 30. As will be discussed more fully, dents, pits, and other surface irregularities can be found and quantified by passing the topological data 162 through appropriate spatial filters. The filtered data 172 is delivered to the display system 30. As will be discussed further, graphical displays, because of the extensive amount of data generated, are the most effective way of presenting the data.

The present invention provides a substantial amount, such as 2000 to 5000, of individual data values corresponding to discrete physical points on the convex surface.

Figure 5:
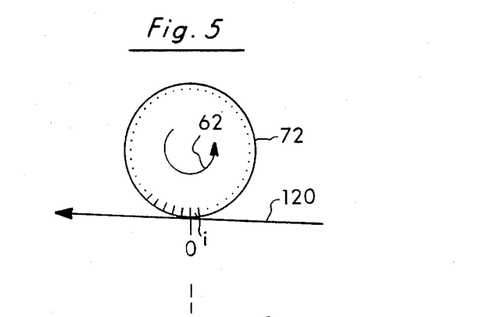
Figure 6:
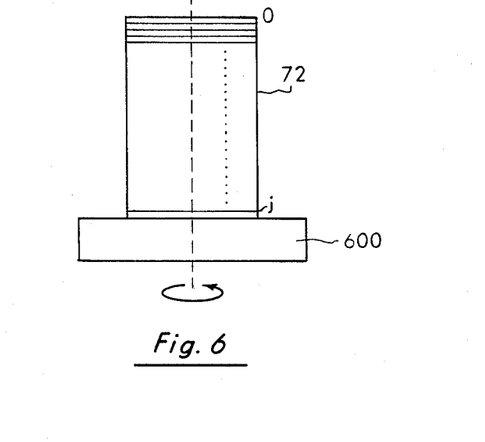

Data Processing—The object 70, such as a can, as shown in FIGS. 5 and 6, can be defined to have a certain number of edges or columns. FIG. 5 shows a number of columns from o to i where the number of edges could, for example, be any suitable number such as 128 columns, 256 columns, or 512 columns. Likewise, the convex surface 72 has a number of rows such as that shown in FIG. 6 from o to j where j could equal 100, 200 or 400 under the teachings of the present invention.

Figure 7:
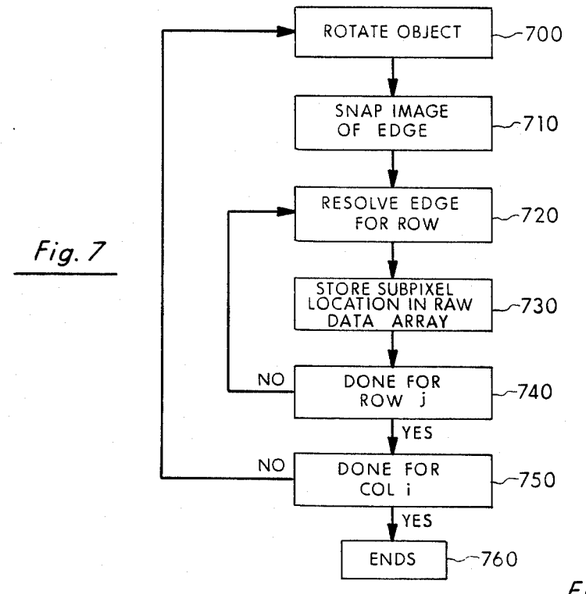
FIG. 7 is the flow diagram for the shadow edge interpolator 150, FIG. 8 sets forth the linear interpolation techniques of the present invention.

The data gathering flow of the present invention as set forth in FIG. 7, will be discussed with reference to FIGS. 5, 6 and 8. The first step in FIG. 7 is to rotate the object 700 and after rotation to snap an image of the edge 710 in camera 140. In FIG. 5, the edge 300 is initially at position 0 and, therefore, a snap of the image at position 0 is taken. The shadow edge taken at position 0 at step 710 actually contains a column of data points one for each of the vertical and discrete locations of the edge as shown in FIG. 6. With respect to the image taken of column 0, the first row 0 has its data point edge resolved.

Figure 8:
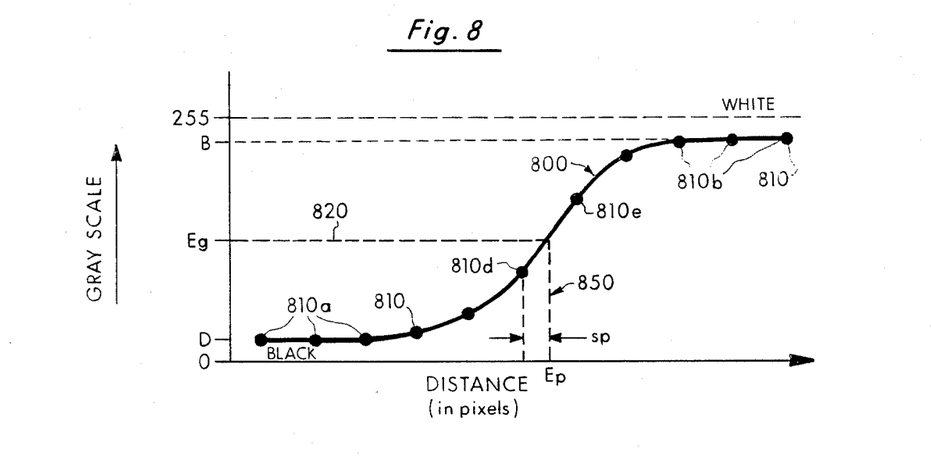

For example, and as shown in FIG. 8, if the shadow edge for column 0, row 0 is shown as curve 800, the determination or resolution of the actual edge could be done in a number of different ways. The present invention utilizes a "linear interpolation" approach to ascertain physical position of the edge from the shadow image 800. Curve 800 represents the shadow edge at one vertical location (i.e., row), as sensed by the camera 140 as an analog signal.

The video signal is digitized into 256 levels, (called gray-levels or gray-values) from 0 to 255. An actual image of a shadow will almost never span the complete 0 to 255 range, as shown in FIG. 8. The three dark pixels 810a are averaged to get the dark reference value, D. The three light pixels 810b are averaged together to obtain an average value, B. These two values, B and D, are averaged together to get the gray value of the edge, Eg, which represents the edge of the shadow.

Using the following definitions:
D = average gray value of dark pixels 810a
B = average gray value of bright pixels 810b
P1 = the gray value of pixel 810d
p2 = the gray value of pixel 810e Then, the gray value of the edge location (defined as Eg) is:

$$Eg = (D+B)/2$$

The subpixel location of the edge, SP, is calculated by:

$$SP = (Eg - P1)/(P2 - P1)$$

And the physical location of the edge, Ep, in the image (which is also the value that is saved in the data file) is:

$$Ep = (\text{location of pixel } 810d) + SP$$

For example, if pixel 810d is located 121 pixels from the edge of the image, and SP is calculated to be = 0.37, then the edge location, Ep, saved to the data file would be 121.37 pixels.

It is to be understood that in the calibration of the optics and data collection 10 of the present invention that an initial physical calibration to a standard object 70 must be made to obtain the actual value of the distance 850. Under the teachings of the present invention, the optics and data collection systems 10 of the present invention, in the preferred embodiment, is such that one pixel equals seven mils on a conventional aluminum beverage can. It is to be understood that the curve 800 is an ideal curve and that the actual raw data is represented by pixels 810.

Returning now to FIG. 7, once the edge location determined 720 for a given row of a shadow, the subpixel location is stored 730 in the raw data array and the routine ascertains whether all the rows are done 740. If not, the process of resolution is repeated until all rows are done. If all of the columns are not done 750, the object 70 is rotated (or rotates) to the next column 700 and the process repeats until all columns are done and the routine ends 760.

As mentioned, this process may take ten seconds to four minutes depending on the size of the object 70 and depending on how many columns and rows are required.

Under the teachings of the present invention, the rotating stage 60 operates asynchronously from the data processing stage 20. The camera 140 provides 60 frames per second and if 128 columns of the object 70 are analyzed, that means in ten seconds (the time for one complete revolution 62), 12.8 columns per second are produced. The camera is operating much faster at 60 frames per second and therefore, approximately five frames for each column are produced. Under the teachings of the present invention, the data processing system 20 selects one of those frames for analysis.

It is possible to design the system such that the data processing system as shown by a line 22 in FIG. 1 synchronously controls the rotation of the stage 60 so that as the stage 60 is rotated a snap of the image of the edge 710 is taken and analyzed before causing the stage 60 to rotate to the next column. Hence, under the teachings of the present invention, the stage 60 can operate either asynchronously or synchronously with the data processing system 20. It is to also be expressly understood that the rotating stage 60 could be driven by a continuous or synchronous motor and the light source 80 could be a strobe lamp which could be selectively flashed over lines 24 by the data processing system 20 to strobe the surface 72 of the object 70.

Figure 10:
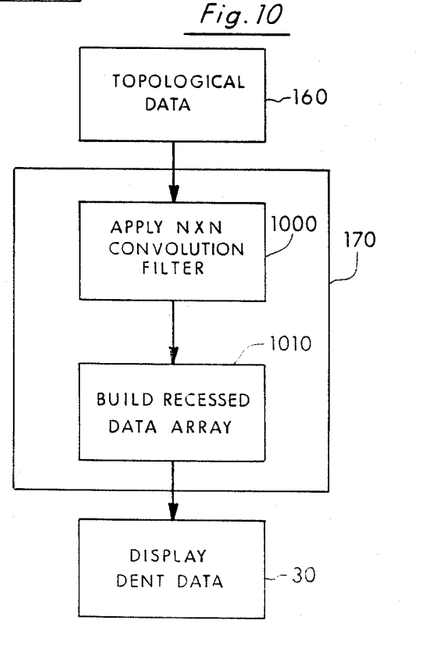

In FIG. 10, details of the spatial filter 170 are shown. An "n" by "n" filter 1000 could be used on the raw profile data to emphasize the rate of change in the surface of the convex object. For example, the convolution filter could emphasize rates of change in the horizontal direction of the object 70, in the vertical direction of the object 70, or in both directions. For example, a suitable convolution filter could be a convolution kernel such as a LaPlacian edge detector. The convolution kernel can be matched to the object or standard set by the user of the system. The convolution filter modifies the raw data to emphasize the characteristic being analyzed (for example vertical dents). By tuning the convolution kernel for quickly changing slopes (i.e., serious dents), slow surface variations and changes are ignored and not displayed. This eliminates background noise.

The output of the convolution filter 1000 is delivered to a module that builds the data array 1010 based upon the output of the convolution filter. The results are then displayed 30.

Figure 11:
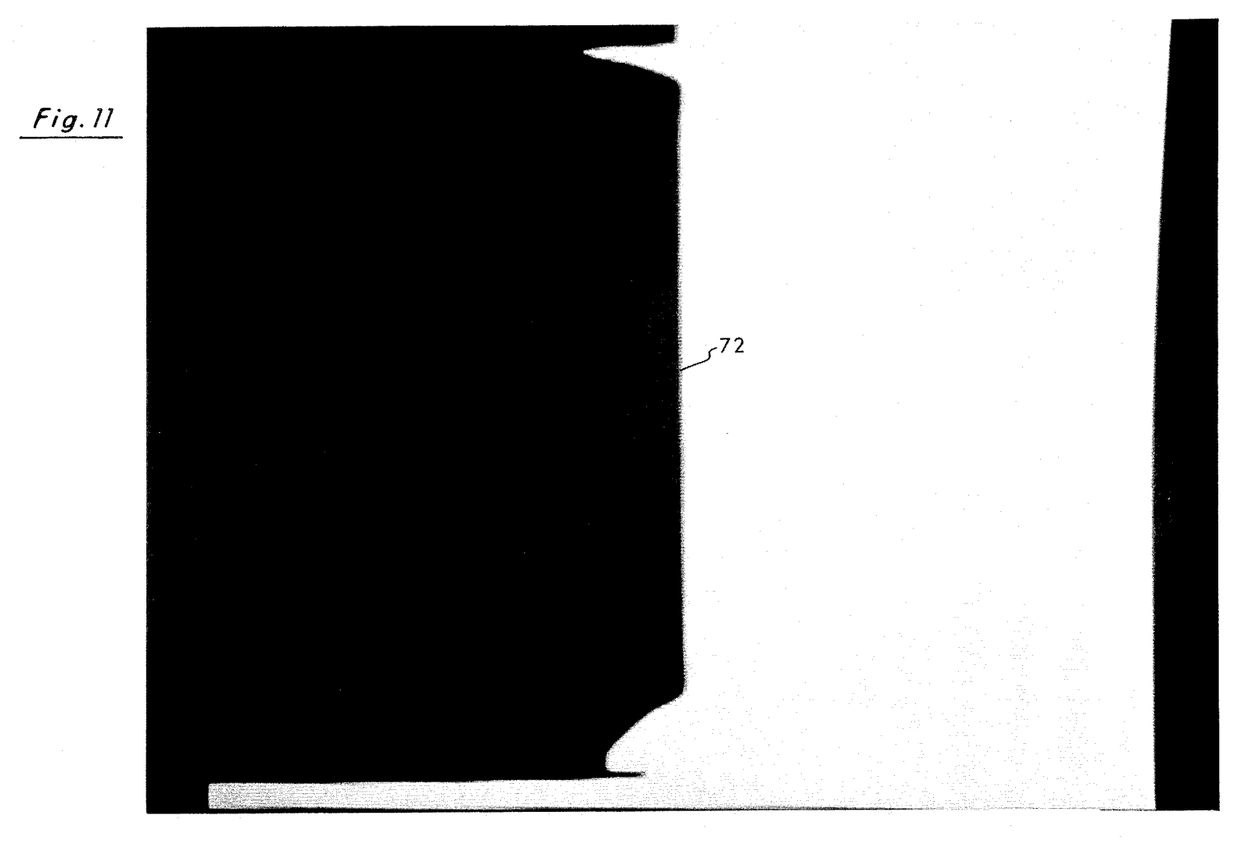
FIG. 11 is a photograph showing the shadow image as seen by the camera 140.

In FIG. 11, the shadow image of a conventional aluminum beverage can edge 72 created by the optics data collection system 10 of the present invention is shown. As mentioned, a large number of these images such as 128 images (corresponding to the columns of the profile) are taken to complete a profile. The data points on each edge constituting the rows are calculated to subpixel accuracy as discussed by the shadow edge interpolator 150.

Figure 9:
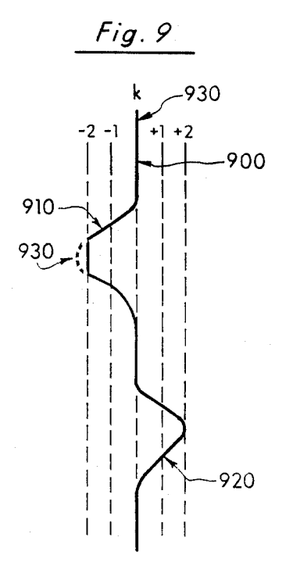
FIG. 9 is an illustration of a truncated range of data in the topological data array for display on a device with limited gray level abilities such as a display monitor, FIG. 10 sets forth the details of the spatial filter 170 of the present invention.
Figure 12:
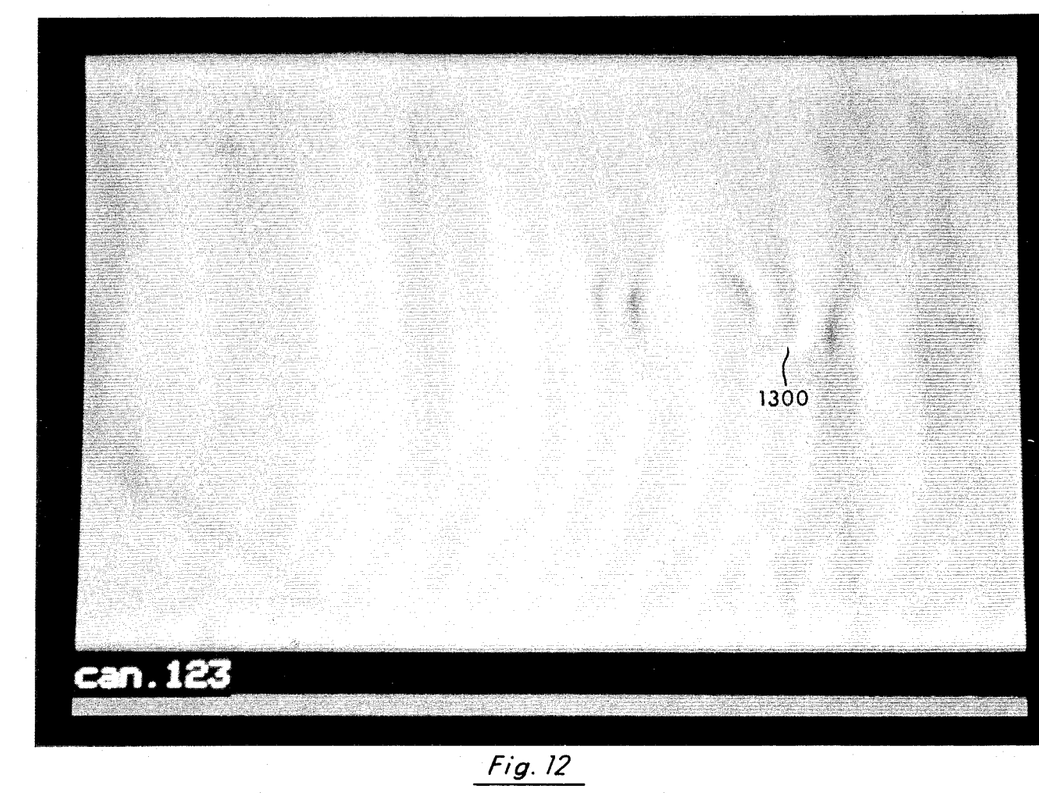
FIG. 12 is an output display of the present invention showing the surface profile of the convex object based on the truncated range of FIG. 9.

FIG. 12 shows how a range of data in the data array can be displayed on a device (such as a video monitor) with a limited number of gray levels. Basically, a small range in the data can be expanded into the number of gray levels available (usually 256) and displayed on the monitor. If the data extends beyond the range selected for display it can be truncated plus or minus, for example two pixels on either side of a gray value, k, as shown in FIG. 9. Dent 1300 is shown. The filtering operation works on the data array, and so is independent of any choices made in this display technique.

Figure 13:
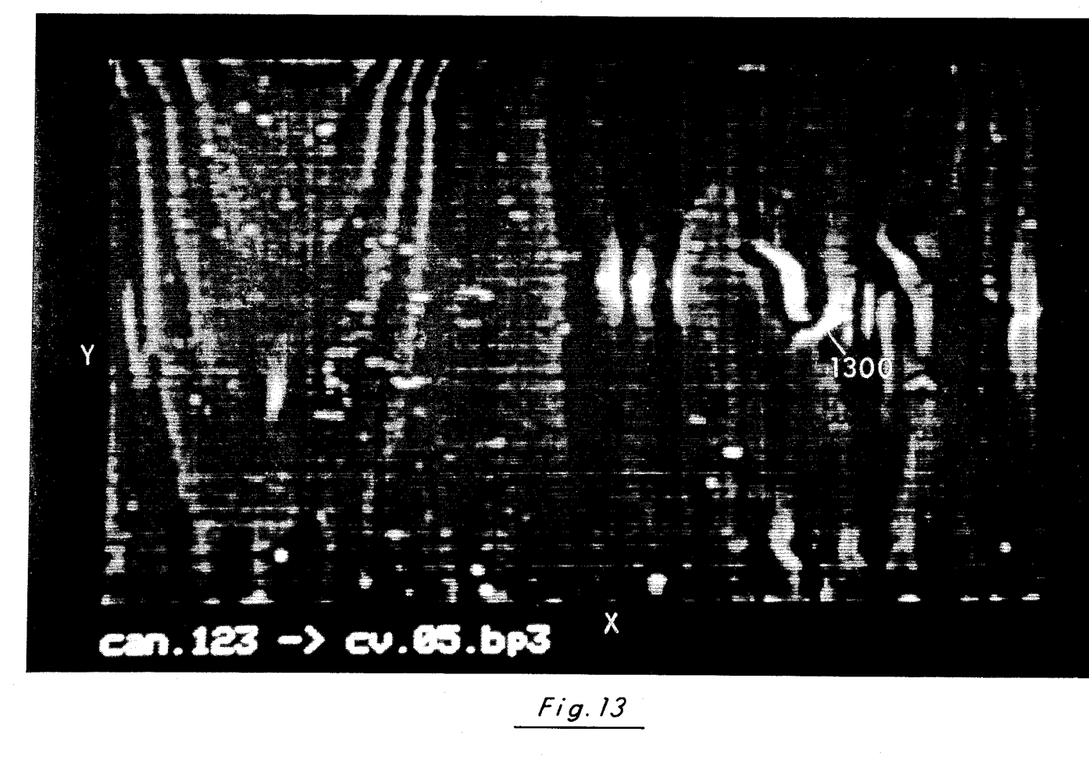
FIG. 13 is an output display of the present invention showing the surface profile of FIG. 12 after spatial filtering.

In FIG. 13, a graphical representation of the raw data of FIG. 12 after spatial filtering 170 by a suitable convolution kernel is displayed. The image is bright where the filter detects rapid changes in the can surface indicating dents. Dent 1300 is shown.

Figure 14:
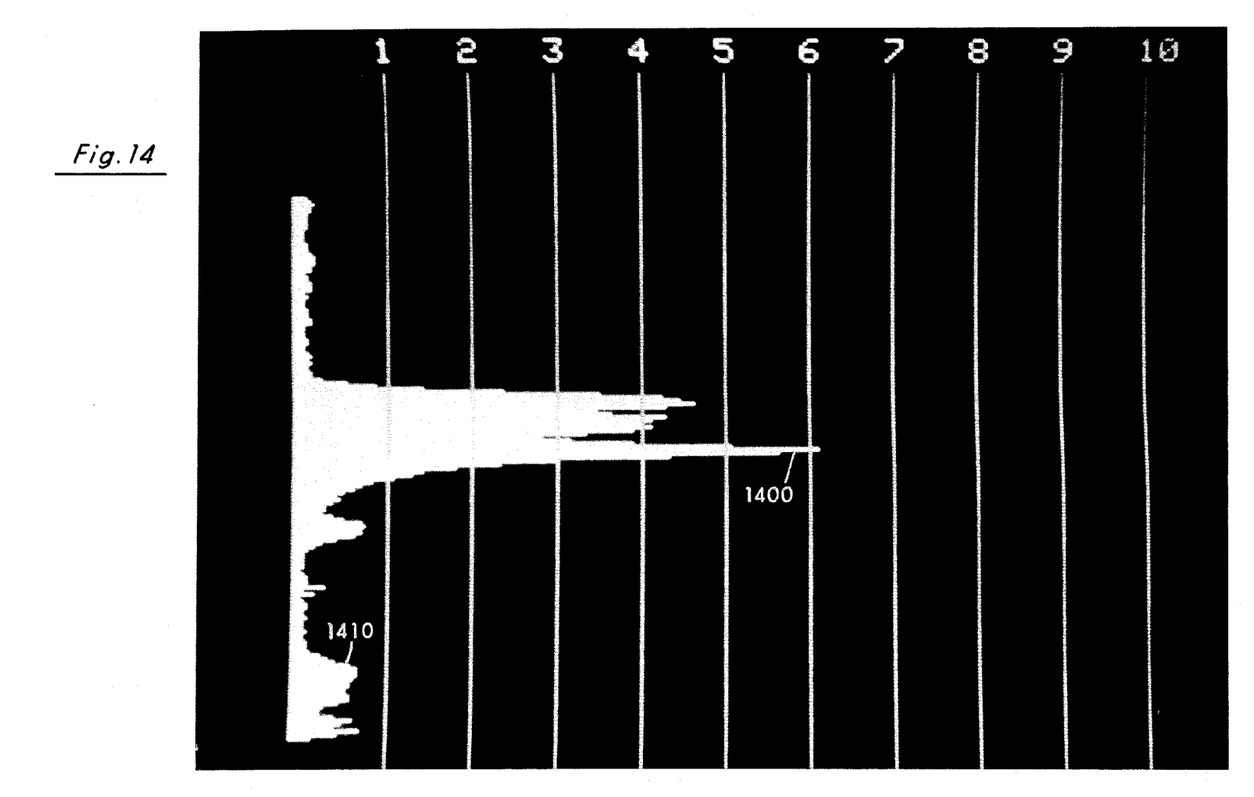
FIG. 14 is a display output of the present invention classifying dents in the surface profile of a convex object according to severity.

In FIG. 14, a display example 30 of an output of the present invention is shown. A convenient scale from 1 to 10 is chosen as a classification indicating severity of dents located vertically along edge 72 of the aluminum beverage can independent of the column location. The vertical scale of the photograph of FIG. 14 represents the vertical height of the can and the dents found at each height throughout all columns of the can is plotted horizontally against the 1 to 10 scale. The photograph shows that dent 1300 has a magnitude 6 as graphically shown at 1400 and several dents of magnitude between 4 and 5. Any suitable range of dent depths could be chosen for display on the scale. The raw topological data 160 can be processed to produce this representation. This graphical representation shown in FIG. 14 enables the system of the present invention to quickly classify cans based upon severity of dents. It also shows the physical location of the dents along the vertical height of the can and, therefore, provides substantial information as to the material make-up of the can and the effect of various manufacturing processes on the can as the can is being manufactured.

While preferred embodiments of the present invention have been shown, it is to be expressly understood that modifications and changes may be made thereto and that the present invention is set forth in the following claims.

We claim:

1. An apparatus for displaying the surface profile of a convex object, said apparatus comprising:
    means (40) for uniformly producing converging white light over an area larger than the area of an edge of said convex object being profiled,
    means (50) opposite said producing means for detecting the shadow image (800) of said edge of said convex object as illuminated by said producing means, said converging white light being focused in said detecting means, said detecting means generating a plurality of pixel outputs for each of a plurality of vertical locations for said shadow image of said edge,
    means (60) for providing movement between said object and said producing and detecting means to provide a plurality of shadow images onto said detecting means corresponding to different edges of said convex object,
    means (20) connected to said detecting means and receptive of said plurality of pixel outputs for determining a sub-pixel distance measurement for each of said plurality of vertical locations, said determining means further being capable of arranging said sub-pixel distance measurements into rows of said surface profile corresponding to individual vertical measurements of said shadow image for one of said edges and into columns of said surface profile corresponding to said plurality of edges, and
    means (30) connected to said determining means and receptive of said row and column measurements for displaying said surface profile.

2. The apparatus of claim 1 wherein said producing means comprises:
    a light source (80) for generating white light,
    an iris (100) containing a diffuser (102) receptive of said white light from said light source for uniformly diffusing said light, and
    means (110) receptive of said diffused light for producing said converging white light over said area.

3. The apparatus of claim 1 wherein said detecting means comprises:
    a cylindrical telescope (130) receptive of said shadow image from said edge of said object, said telescope having a field of view in the horizontal direction of said image at least one-half the field of view in the vertical direction, and
    a camera (140) receptive of said shadow image through said cylindrical telescope for generating said plurality of pixel outputs.

4. The apparatus of claim 1, wherein said determining means comprises:
    an interpolator (150) receptive of said plurality of pixel outputs for determining said sub-pixel distance measurement,
    means (160) receptive of said sub-pixel distance measurements for assembling an X-Y surface profile of the distance measurements, and
    means (170) receptive of said X-Y surface profile for spatially filtering said X-Y surface profile according to a predetermined convolution kernel in order to emphasize desired variation parameters.

5. The apparatus of claim 4 wherein said interpolator comprises means for determining the actual edge distance of said shadow image through linear interpolation between the two pixels immediately above and below the actual edge of the shadow.

6. An apparatus for displaying the surface profile of a convex object, said apparatus comprising:
    means (40) for uniformly producing converging white light over an area larger than the area of an edge of said convex object being profiled,
    means (50) opposite said producing means for detecting the shadow image (800) of said edge of said convex object as illuminated by said producing means, said converging white light being focused in said detecting means, said detecting means generating a plurality of pixel outputs for each of a plurality of vertical locations for said shadow image of said edge,
    means in said detecting means for providing a field of view in the horizontal direction of said edge which is at least one-half the field of view along the vertical direction of said edge thereby magnifying dimensional variations in said edge,
    means (60) for providing movement between said object and said producing and detecting means to provide a plurality of shadow images onto said detecting means corresponding to different edges of said convex object, means (20) connected to said detecting means and receptive of said plurality of pixel outputs for determing a sub-pixel distance meaurement for each of said plurality of vertical locations, said determining means further being capable of arranging said sub-pixel distance measurements into rows of said surface profile corresponding to individual vertical measurements of said shadow image for one of said edges and into columns of said surface profile corresponding to said plurality of edges, and means (30) connected to said determining means and receptive of said row and column measurements for displaying said surface profile.

7. An apparatus for displaying the surface profile of a convex object, said apparatus comprising:

means (40) for uniformly producing converging white light over an area larger than the area of an edge of said convex object being profiled, means (50) opposite said producing means for detecting the shadow image (800) of said edge of said convex object as illuminated by said producing means, said converging white light being focused in said detecting means, said detecting means generating at least four pixel outputs for each of a plurality of vertical locations for said shadow image of said edge, means in said detecting means for providing a field of view in the horizontal direction of said edge which is at least twice the field of view in the vertical direction of said edge thereby magnifying variations in said edge, means (60) for providing movement between said object and said producing and detecting means to provide a plurality of shadow images onto said detecting means corresponding to different edges of said convex object, means (20) connected to said detecting means and receptive of said plurality of pixel outputs for determining a sub-pixel distance measurement for each of said plurality of vertical locations, said determining means further being capable of arranging said sub-pixel distance measurements into rows of said surface profile corresponding to individual vertical measurements of said shadow image for one of said edges and into columns of said surface profile corresponding to said plurality of edges, and means (30) connected to said determining means and receptive of said row and column measurements for displaying said surface profile.

8. An apparatus for displaying the severity of dents in the surface of a convex object according to a predetermined classification, said apparatus comprising:

means (40) for uniformly producing converging white light over an area larger than the area of an edge of said convex object being profiled, means (50) opposite said producing means for detecting the shadow image (800) of said edge of said convex object as illuminated by said producing means, said converging white light being focused in said detecting means, said detecting means generating a plurality of pixel outputs for each of a plurality of vertical locations for said shadow image of said edge, means (60) for providing movement between said object and said producing and detecting means to provide a plurality of shadow images onto said detecting means corresponding to different edges of said convex object, means (20) connected to said detecting means and receptive of said plurality of pixel outputs for determining a sub-pixel distance measurement for each of said plurality of vertical locations, said determining means further being capable of classifying dents based upon said sub-pixel distance measurements into said predetermined classification, and means (30) connected to said determining means and receptive of said classification of dents for displaying said severity of said dents according to said classification.

9. A method for displaying the surface profile of a convex object, said apparatus comprising:

uniformly converging white light over an area larger than the area of an edge of said convex object being profiled, detecting the shadow image of the edge of said convex object as illuminated by said white light, generating a plurality of pixel outputs for each of a plurality of vertical locations for said shadow image of said edge in response to the detection of the shadow image, providing movement to the object to provide a plurality of shadow images corresponding to different edges of said convex object, determining a sub-pixel distance measurement for each of said plurality of vertical locations, arranging said sub-pixel distance measurements into rows of said surface profile corresponding to individual vertical measurements of said shadow image for one of said edges and into columns of said surface profile corresponding to said plurality of edges, and displaying said surface profile.

10. A method for displaying the surface profile of a convex object, said apparatus comprising:

uniformly converging white light over an area larger than the area of an edge of said convex object being profiled, detecting the shadow image of the edge of said convex object as illuminated by said white light, generating a plurality of pixel outputs for each of a plurality of vertical locations for said shadow image of said edge in response to the detection of the shadow image, providing a field of view in the horizontal direction of said edge which is at least one-half the field of view along the vertical direction of said edge thereby magnifying dimensional variations in said edge, providing movement to the object in order to provide a plurality of shadow images corresponding to different edges of said convex object, determining a sub-pixel distance measurement for each of said plurality of vertical locations, arranging said sub-pixel distance measurements into rows of said surface profile corresponding to individual vertical measurements of said shadow image for one of said edges and into columns of said surface profile corresponding to said plurality of edges, and displaying said surface profile.

11. A method for displaying the surface profile of a convex object, said apparatus comprising:

uniformly converging white light over an area larger than the area of an edge of said convex object being profiled, detecting the shadow image of said edge of said convex object as illuminated by said white light, generating at least four pixel outputs for each of a plurality of vertical locations for said shadow image of said edge, providing a field of view in the horizontal direction of said edge which is at least one-half the field of view in the vertical direction of said edge thereby magnifying variations in said edge, providing movement to the object to provide a plurality of shadow images onto said detecting means corresponding to different edges of said convex object, determining a sub-pixel distance measurement for each of said plurality of vertical locations, arranging said sub-pixel distance measurements into rows of said surface profile corresponding to individual vertical measurements of said shadow image for one of said edges and into columns of said surface profile corresponding to said plurality of edges, and displaying said surface profile.

12. A method for displaying the severity of dents in the surface of a convex object according to a predetermined classification, said apparatus comprising:

uniformly converging white light over an area larger than the area of an edge of said convex object being profiled, detecting the shadow image of said edge of the convex object, generating a plurality of pixel outputs for each of a plurality of vertical locations for said shadow image of said edge, providing movement to said object to provide a plurality of shadow images corresponding to different edges of said convex object, determining a sub-pixel distance measurement for each of said plurality of vertical locations, classifying dents based upon said sub-pixel distance measurements into said predetermined classification, and displaying said severity of said dents according to said classification.

* * * * *